United States Patent
Brianza et al.

(10) Patent No.: US 9,579,158 B2
(45) Date of Patent: Feb. 28, 2017

(54) SURGICAL INSTRUMENT

(75) Inventors: Stefano Brianza, Davos Dorf (CH);
Ronald Schwyn, Davos Glaris (CH)

(73) Assignee: AO Technology AG, Chur (CH)

( * ) Notice: Subject to any disclaimer, the term of this patent is extended or adjusted under 35 U.S.C. 154(b) by 473 days.

(21) Appl. No.: 13/995,465

(22) PCT Filed: Dec. 24, 2010

(86) PCT No.: PCT/CH2010/000330
§ 371 (c)(1),
(2), (4) Date: Aug. 30, 2013

(87) PCT Pub. No.: WO2012/083468
PCT Pub. Date: Jun. 28, 2012

(65) Prior Publication Data
US 2013/0338669 A1   Dec. 19, 2013

(51) Int. Cl.
*A61B 17/00* (2006.01)
*A61B 19/00* (2006.01)
(Continued)

(52) U.S. Cl.
CPC ............ *A61B 19/46* (2013.01); *A61B 5/4509* (2013.01); *A61B 17/1615* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 4,137,002 A | * | 1/1979 | Barker et al. | 408/59 |
| 2005/0131415 A1 | * | 6/2005 | Hearn et al. | 606/80 |

FOREIGN PATENT DOCUMENTS

| | | |
|---|---|---|
| DE | 10018769 A1 | 10/2001 |
| WO | 02/09598 A2 | 2/2002 |
| WO | 2008/052367 A1 | 5/2008 |

OTHER PUBLICATIONS

International Preliminary Report on Patentability dated Jun. 25, 2013 in corresponding International Application No. PCT/CH2010/000330, filed Dec. 24, 2010.

* cited by examiner

*Primary Examiner* — Sameh Boles
(74) *Attorney, Agent, or Firm* — Rankin, Hill & Clark LLP

(57) ABSTRACT

Surgical instrument (1) comprising a longitudinal shaft (2) with a tip portion (3), a rear portion (4) and a longitudinal axis (5) and rotatable in the clock-wise and in the counter-clockwise direction around the longitudinal axis (5), said surgical instrument (1) further comprising: A) first means (6) for drilling a hole in a bone by rotation of the shaft (2) in one of the two directions; B) second means (7) for crushing bone tissue when the shaft (2) rotates in the other of the two directions; and C) a torque sensor (10) coupled to the shaft (2). Method for measuring the local mechanical resistance of a porous body comprising the steps of: a) drilling a hole to a desired depth into a porous body by advancing and rotating the shaft (2) in a first sense of rotation, preferably clockwise so that said first means (6) are active; b) hammering the shaft (2) gently further into the porous body as far as the tip portion (3) of the shaft (2) has reached a desired measuring position; and c) performing the torque measurement by rotating the shaft (2) in the opposite second sense of rotation, preferably counter-clockwise so that said second means (7) are active.

13 Claims, 1 Drawing Sheet

(51) Int. Cl.
*A61B 5/00* (2006.01)
*A61B 17/16* (2006.01)
*A61B 17/88* (2006.01)

(52) U.S. Cl.
CPC .......... *A61B 17/1664* (2013.01); *A61B 17/88* (2013.01); *A61B 90/06* (2016.02); *A61B 17/1668* (2013.01); *A61B 2090/064* (2016.02); *A61B 2090/066* (2016.02)

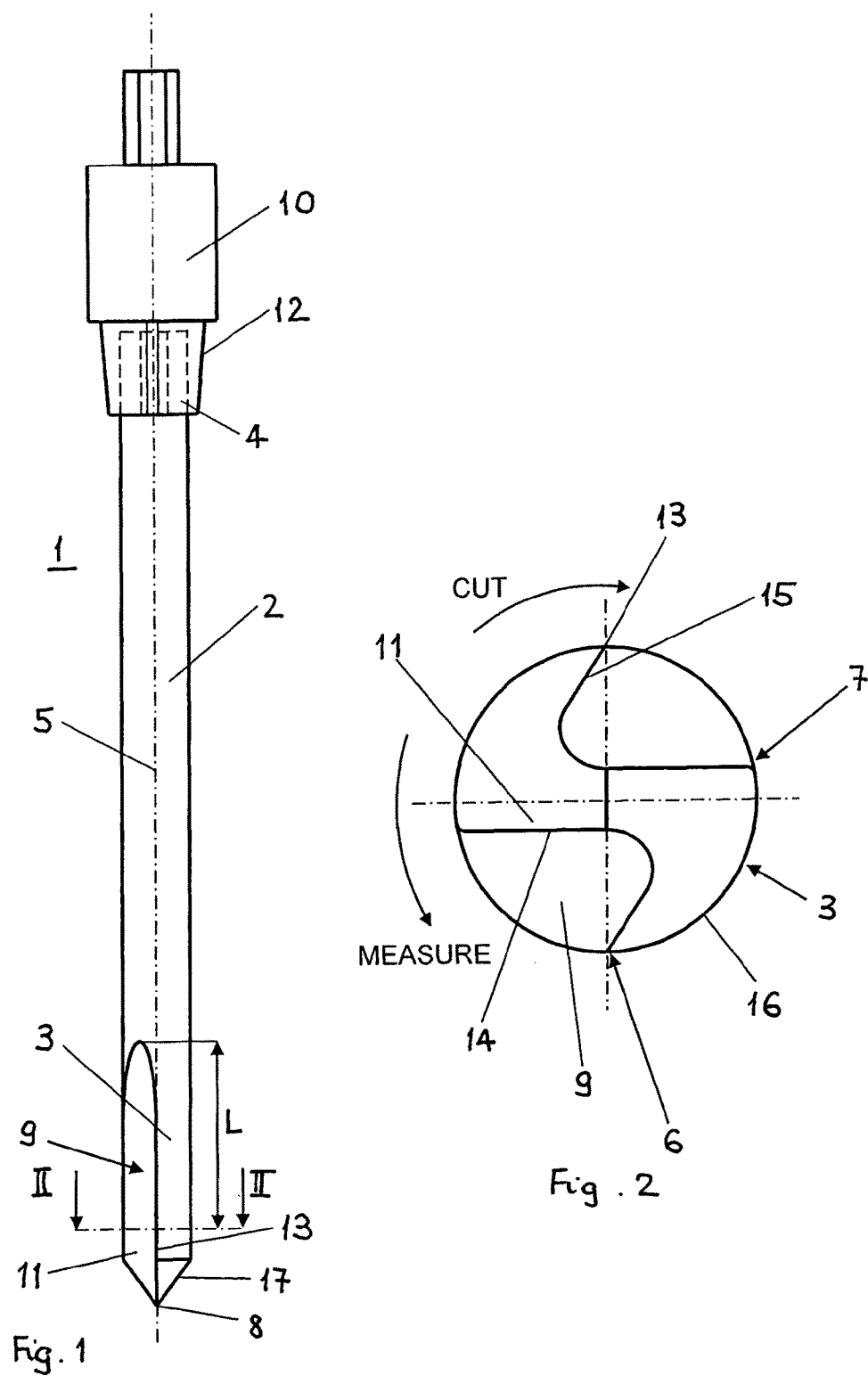

SURGICAL INSTRUMENT

BACKGROUND OF THE INVENTION

1. Field of the Invention

The invention relates to a surgical instrument, to a method for measuring the local mechanical resistance of a porous body and to the use of the surgical instrument for estimating the quality of cancellous bone.

Known probes for measuring the mechanical resistance of porous bone commonly comprise a cannulated probe that is slid on a K-wire previously inserted in the bone. However, during insertion the K-wire is mostly slightly deformed resulting in a variable contact area between the K-wire and the inner surface of the cannulation of the probe. The larger being the contact area between the K-wire and the probe the more being the K-wire deformed (resulting in a force component normal to the inner probe surface) the higher is the friction between the K-wire and the probe. The higher the friction between probe and the K-wire is the higher will be (artificially) the recorded torque. The lower the bone mineral density is the higher is the weight of this bias. Disregarding this varying frictional torque can lead the surgeon to take a wrong decision.

2. Description of the Related Art

From WO 2008/052367 a device for determining the local mechanical resistance inside of a porous body having a variable density and/or porosity is known. This known device comprises a tool with a shank having a tip with blades that allow to measure the local mechanical resistance of the porous body after pushing the tip into a porous structure at the bottom of a predrilled hole and rotating the tool about its longitudinal axis. Particularly, when measuring the local mechanical resistance of porous bone in the cancellous bone tissue a bore hole has to be predrilled through the harder cortical bone tissue surrounding the cancellous bone tissue. Therefore, this known device shows the disadvantage that a hole has to be previously drilled into the bone by using a separate tool.

BRIEF SUMMARY OF THE INVENTION

It is an object of the invention to provide a surgical instrument allowing to drill a hole in cancellous bone and to assess the cancellous bone quality by using a single instrument.

The invention solves the posed problem with a surgical instrument displaying the features of claim 1, with a method for measuring the local mechanical resistance of a porous body displaying the features of claim 17 and with the use of the surgical instrument for estimating the quality of cancellous bone displaying the features of claim 20.

The advantages of the surgical instrument essentially are:
the ease to use due to a single instrument to drill a hole into a bone and to measure the bone quality;
to avoid the friction between the probe and a guide wire of known probes;
the possibility of downsizing the instrument; and
to have dimension compatibility with future implant design making the redesign of the probe and thresholds assessment virtually not necessary.

Preferably, the cortex of the bone is opened by using a separate drill bit. Thus, the torque measurement is not affected by the friction between the surgical instrument and the cortex so that by using the surgical instrument the resistance caused by the cancellous bone only is measured.

The surgical instrument according to the invention is particularly suitable for measuring the local mechanical resistance of a porous body where the porous structure is variable in density and structure and especially where the surface of the body has a much harder surface layer, such as bone.

The measurement of the local mechanical resistance is performed by rotating the shaft around its longitudinal axis in a given angular direction (for example the standard clockwise direction used worldwide for cutting tools) so that the tip at the front of the shaft is able to cut the bone and once the shaft is rotated around its longitudinal axis in the opposite angular direction (for example in the counter clockwise direction) the tip is able to perform a breakaway torque measurement. The torque measurement is performed by firmly connecting the shaft to a torque sensor.

The double feature is made possible by modifying the tip design such that the cutting edges face the cutting direction and the flat surfaces face the measuring direction. The difference between cutting and measuring is in the interaction between the tip and the bone: the cutting edge separates the bone tissue into parts with a sharp edge while the measuring surface deforms the bone tissue until if fails. The torque signal retrievable from the flat surface can be reasonably expected to be significantly higher than that retrievable from the cutting edge in all materials.

Furthermore, the flat surface will not affect the wire cutting properties and the cutting edge will not affect the torque measurement.

For measuring the local mechanical resistance in the cancellous bone the surgeon firstly drills a hole through the cortical bone tissue and if desired to a certain depth into the cancellous bone by rotating the shaft in a first angular direction, takes an x-ray to check the position of the tip and, when appropriate, gently hammers the shaft further into the bone tissue till the measuring position of the tip is reached. Subsequently, the surgeon rotates the shaft in the second opposite angular direction and performs a measurement.

During the measurement the part of shaft which is not involved in the measurement is surrounded by bone tissue only. Theoretically, it can be assumed that the friction between shaft and the hole produced in the cancellous bone will generate a torque of at least one order of magnitude lower than that recorded by the measurement of the local mechanical resistance. The friction between the bone tissue and the metallic shaft is much smaller than the metal to metal friction. Furthermore, the contact surface is reduced because it is extremely difficult to drill a perfectly cylindrical hole.

The preferred material for the shaft of the surgical instrument is 316L stainless medical steel.

In a special embodiment of the surgical instrument the shaft is in the form of a K-wire or rod.

In a further embodiment of the surgical instrument the first and/or second means are located at the tip portion of the shaft.

In another embodiment of the surgical instrument the first means comprises one or more sharp cutting edges. This allows to drill a hole into the cancellous bone tissue.

In another embodiment of the surgical instrument the second means comprises one or more crusher jaws extending in a direction along the longitudinal axis, preferably being integral with the first means and arranged oppositely to said cutting edges. The one or more crusher jaws allow to measure the torque produced by rotation of the shaft in the opposite direction when impacted into the cancellous bone in front of the previously drill hole.

In another embodiment of the surgical instrument said tip portion comprises one or more flutes penetrating into the shaft and extending in a direction along the longitudinal axis and each flute forming a cutting edge extending at least on a front surface of said tip portion. Alternatively, the tip portion can be configured as a spade or flat drill bit, wherein the portion of the blade which is oppositely to the cutting edges forms the crusher jaw.

In again another embodiment of the surgical instrument said tip portion comprises two flutes arranged at an angle of 180° relative to each other in a cross section orthogonal to said longitudinal axis.

In a further embodiment of the surgical instrument the one or more crusher jaws each have a crushing surface located in one flute oppositely to a cutting edge.

In a further embodiment of the surgical instrument said tip portion comprises a peripheral surface and wherein each crushing surface encloses an angle equal to or greater than 90° with said peripheral surface. The edges formed at the intersection line of the crushing surface and the peripheral surface can be rounded or beveled.

In again a further embodiment of the surgical instrument each flute forms a lateral cutting edge extending parallel to said longitudinal axis of said shaft.

In yet a further embodiment of the surgical instrument said tip portion comprises a peripheral surface and wherein each flute defines a cutting face which encloses an acute cutting angle with said peripheral surface.

In another embodiment of the surgical instrument said tip portion comprises a front surface that encloses an acute angle with said cutting face.

In another embodiment the surgical instrument further comprises a resilient means able to rotate the shaft in the second direction for crushing bone tissue. For the crushing action a rotation of the shaft about 120 degree is enough. This can be performed by the resilient means or alternatively manually. The torque measured according to the region of interest amounts indicatively to 1-4 Nm in the femur and to 0.5-1.2 Nm in the humerus.

In another embodiment of the surgical instrument the torque sensor comprises strain gauges attached to the shaft.

In yet another embodiment of the surgical instrument a signal related to the torque measured by the torque sensor is transferred to an indicator means by means of wireless telemetry.

In still another embodiment of the surgical instrument said torque sensor measures the torque exerted onto the shaft by the second means for crushing bone tissue.

In a special embodiment the method further comprises before step b) the sub-step of controlling the position of the tip portion of the shaft by using an X-ray device.

In a further embodiment of the method said porous body is a bone or bone fragment, preferably a proximal femur and the method further comprising after step c) the step of deciding on the basis of the measured value of the torque measured under step c) if:
   i. the measured value of the torque is high enough so as to indicate a sufficient bone density and/or porosity to implant a hip screw or a hip blade; or
   ii. the measured value of the torque is in a range where a bone cement is to be applied to augment the bone tissue around the shaft of the hip screw or hip blade; or
   iii. the measured value of the torque is very low so that a hip prosthesis has to be implanted.

A BRIEF DESCRIPTION OF THE DRAWINGS

A special embodiment of the invention will be described in the following by way of example and with reference to the accompanying drawings in which:

FIG. 1 illustrates a side view of an embodiment of the surgical instrument according to the invention; and FIG. 2 illustrates a sectional view of the tip portion along line II-II in FIG. 1.

DETAILED DESCRIPTION OF THE INVENTION

FIGS. 1 and 2 illustrate an embodiment of the surgical instrument 1 including a longitudinal shaft 2 with a longitudinal axis 5, a tip portion 3 and a rear portion 4, first means 6 for drilling a hole in a bone by rotating the shaft 2 in the clockwise direction about its longitudinal axis 5, second means 7 for crushing bone tissue by rotating the shaft 2 in the counter-clockwise direction about its longitudinal axis 5 and a torque sensor 10 coupled to the shaft 2. The torque sensor 10 is configured to measure the breakaway torque of the bone tissue when the shaft 2 is rotated in the counter-clockwise direction.

The shaft 2 is essentially circular cylindrical and can have the size of a K-wire. The rear portion 4 of the shaft 2 can be configured with a polygonal, e.g. hexagonal cross section so that the shaft 2 can be coupled to a torque sensor 10 in a rotationally and axially fixed manner. The torque sensor 10 can be integral with a drive unit or can be provided with a polygonal, e.g. hexagonal bolt extending coaxially at the end of the torque sensor 10 which is opposite to the shaft 2 so that the shaft 2 can be fixed to the torque sensor 10 e.g. by means of a drill chuck 12 coupled to the torque sensor 10. The assembly comprising the shaft 2 and the torque sensor 10 can be coupled to a drive unit. Alternatively, the torque sensor 10 can comprise strain gauges attached to the shaft 2. The electric power supplied to the strain gauges can be transmitted to the strain gauges by means of slip rings or wireless telemetry. The signal related to the torque measured by the strain gauges of the torque sensor 10 can be transmitted to an indicator means and/or other electronic equipment, e.g. a computer by means of said slip rings or wireless telemetry as well. Furthermore, an electronic analog-digital converter (A/D converter) can be attached to the shaft 2.

The tip portion 3 has a pointed tip 8, a peripheral surface 16, a front surface 17 and two flutes 9 arranged at an angle of 180° relative to each other in a cross section along line II-II in FIG. 1. Each of the two flutes 9 is axially open at the front surface 17 of the tip portion 8 and extends from the front surface 17 in a direction along the longitudinal axis 5 of the shaft 2 on a length L measured from said pointed tip 8 towards the rear portion 4 of said shaft 2. Each flute 9 defines a concave surface that intersects the peripheral surface 16 and the front surface 17 of the tip portion 3. The cutting edge 13 extends frontally along the intersection line of said concave surface with the front surface 17 of the tip portion 3 and extends laterally along the intersection line of said concave surface with the peripheral surface 16 of the tip portion 3. The lateral section of the cutting edge 13 extends parallel to the longitudinal axis 5 of said shaft 2 so that the shaft 2 can be gently hammered further into the bone tissue as far as the measuring position of the tip portion 3 is reached.

The concave surface defined by each flute 9 defines a cutting face 15 facing the cutting direction and enclosing an acute cutting angle with the peripheral surface 16. Furthermore, the front surface 17 of the tip portion 3 can enclose the same acute angle with said cutting face 15. The cutting edges 13 defined by the two flutes 9 form the first means 6 for drilling a hole in a bone by rotating the shaft 2 in the clockwise direction about its longitudinal axis 5.

The second means 7 for crushing bone tissue by rotating the shaft 2 in the counter-clockwise direction about its longitudinal axis 5 comprise two crusher jaws 11 extending in a direction along the longitudinal axis 5. Each of the crusher jaws 11 has a crushing surface 14 that is part of said concave surface defined by each flute 9 and located oppositely to the respective cutting face 15. Thereby, the crushing surfaces 14 face the crushing direction, which is in the present embodiment the counter-clockwise direction. The crusher jaws 11 are integral with the tip portion 3 of the shaft 2 and with the first means 6. Each crusher jaw 11 is arranged on a part of the tip portion 3 that is located between two flutes 9 and oppositely to the respective cutting edge 13. Each crushing surface 14 can enclose an angle equal to or greater than 90° with the peripheral surface 16 of the tip portion 3.

EXAMPLE 1

During the proximal locking procedure of an intramedullary nail implanted in the proximal femur the following steps are performed:
1) fastening a suitable aiming guide to the proximal end of the intramedullary nail;
2) inserting a trocar combination including a tissue protection sleeve together with a drill bushing and a trocar into the aiming guide in a desired position;
3) attaching a guide wire aiming device to the aiming guide;
4) adjusting the insertion depth of the intramedullary nail by using an X-ray device;
5) adjusting the orientation of the intramedullary nail in a true lateral position of the X-ray device;
6) performing a stab incision in the area of the trocar tip and advancing the trocar combination through the soft tissue as far as the lateral cortical bone surface;
7) removing the trocar;
8) opening the lateral cortex;
9) inserting the shaft 2 of the surgical instrument 1 into the drill bushing;
10) drilling a hole to a desired depth into the femoral neck and the femoral head by advancing and rotating the shaft 2 clockwise;
11) controlling the position of the tip 8 of the shaft 2 by using the X-ray device;
12) hammering the shaft 2 gently as far as it reaches the recommended distance to the surface of the femoral head, so that the tip 8 of the shaft 2 is exactly positioned at the planned position of the tip of a blade or screw to be inserted into the femoral neck and the femoral head;
13) performing the measurement of the torque related to the bone density and or porosity by rotating the shaft 2 counter clockwise;
14) deciding on the basis of the measured value of the torque measured under the previous step if:
   a) the measured value of the torque is high enough so as to indicate a sufficient bone density and/or porosity to implant a hip screw or a hip blade; or
   b) the measured value of the torque is in a range where a bone cement is to be applied to augment the bone tissue around the shaft of the hip screw or hip blade; or
   c) the measured value of the torque is very low so that a hip prosthesis is to be implanted. In this case the intramedullary nail has to be explanted and a surgical procedure for implanting a hip prosthesis has to be performed;
15) selecting an appropriate hip screw or blade;
16) removing the drill bushing;
17) reaming the lateral cortex and the cancellous bone if necessary for insertion of the hip screw or blade;
18) applying bone cement if necessary;
19) inserting the hip screw or blade; and
20) removing the aiming guide.

While various descriptions of the present invention are described above, it should be understood that the various features can be used singly or in any combination thereof. The scope of the present invention is accordingly defined as set forth in the appended claims.

The invention claimed is:

1. A surgical instrument comprising a longitudinal shaft with a tip portion, a rear portion and a longitudinal axis, said shaft being selectively rotatable in two directions around the longitudinal axis, said two directions being clockwise and counterclockwise, said surgical instrument further comprising:
   one or more sharp cutting edges extending at least on a front surface of the tip portion of the shaft for drilling a hole in a bone by rotation of the shaft in one of the two directions;
   one or more crusher jaws arranged on the tip portion and extending along the longitudinal axis of the shaft for crushing bone tissue by rotation of the shaft in the other of the two directions; and
   a torque sensor coupled to the shaft, said torque sensor configured to measure torque exerted onto the shaft when the shaft is rotated in the other of the two directions and the crusher jaws are crushing bone tissue.

2. The surgical instrument according to claim 1, wherein the shaft is in the form of a K-wire or rod.

3. The surgical instrument according to claim 1, wherein said tip portion comprises one or more flutes penetrating into the shaft and extending in a direction along the longitudinal axis, and wherein each flute forms one of the one or more sharp cutting edges extending at least on a front surface of said tip portion.

4. The surgical instrument according to claim 3, wherein said tip portion comprises two flutes arranged at an angle of 180° relative to each other in a cross section orthogonal to said longitudinal axis.

5. The surgical instrument according to claim 3, wherein the one or more crusher jaws each have a crushing surface located in one flute oppositely to a cutting edge.

6. The surgical instrument according to claim 5, wherein said tip portion comprises a peripheral surface and wherein each crushing surface encloses an angle equal to or greater than 90° with said peripheral surface.

7. The surgical instrument according to claim 3, wherein each flute forms a lateral cutting edge extending parallel to said longitudinal axis of said shaft.

8. The surgical instrument according to claim 3, wherein said tip portion comprises a peripheral surface and wherein each flute defines a cutting face which encloses an acute cutting angle with said peripheral surface.

9. The surgical instrument according to claim 8, wherein said tip portion comprises a front surface that encloses an acute angle with said cutting face.

10. The surgical instrument according to claim 1, further comprising a resilient means for rotating the shaft in the second direction for crushing bone tissue.

11. The surgical instrument according to claim 1, wherein the torque sensor comprises strain gauges attached to the shaft.

12. The surgical instrument according to claim 1, wherein a signal related to torque measured by the torque sensor is transferred to an indicator means by wireless telemetry.

13. The surgical instrument according to claim 1, wherein the one or more crusher jaws are integral with and arranged oppositely to said cutting one or more sharp cutting edges.

* * * * *